United States Patent [19]
Del Fabbro

[11] Patent Number: 5,272,963
[45] Date of Patent: Dec. 28, 1993

[54] ARRANGEMENT FOR MEASURING MOISTURE IN OVENS, IN PARTICULAR FOOD COOKING OVENS

[75] Inventor: Claudio Del Fabbro, Pordenone, Italy

[73] Assignee: Zanussi Grandi Impianti S.p.A., Italy

[21] Appl. No.: 52,505

[22] Filed: Apr. 26, 1993

[30] Foreign Application Priority Data

Apr. 29, 1992 [IT] Italy ............................ PN92A000036

[51] Int. Cl.$^5$ ................................................ A21B 1/08
[52] U.S. Cl. .......................................... 99/468; 99/330; 99/331; 99/470; 99/476; 126/20; 126/21 A; 219/400; 219/401
[58] Field of Search ................. 99/331, 330, 332, 333, 99/325, 345–347, 451, 467, 468, 473, 476, 470, 483; 126/20, 21 A; 219/400, 401; 426/510, 523

[56] References Cited

U.S. PATENT DOCUMENTS

| | | | |
|---|---|---|---|
| 4,455,924 | 6/1984 | Wenzel | 126/21 A |
| 4,462,383 | 7/1984 | Henke et al. | 99/468 |
| 4,655,192 | 4/1987 | Jovanovic | 126/20 |
| 4,700,685 | 10/1987 | Miller | 99/330 |
| 4,776,265 | 10/1988 | Ojima | 99/468 |
| 4,823,766 | 4/1989 | Violi | 99/476 |
| 4,870,254 | 9/1989 | Arabori et al. | 219/400 |
| 4,876,426 | 10/1989 | Smith | 219/401 |
| 4,884,553 | 12/1989 | Schwarzbacker | 126/21 A |
| 5,014,679 | 5/1991 | Childs et al. | 99/476 |
| 5,029,519 | 7/1991 | Boyen | 219/400 |

FOREIGN PATENT DOCUMENTS 0335796 10/1989 European Pat. Off. ............ 99/468

Primary Examiner—Timothy F. Simone
Attorney, Agent, or Firm—Pearne, Gordon, McCoy & Granger

[57] ABSTRACT

An arrangement measures humidity in ovens, in particular fan-assisted food-cooking ovens which have a cooking cavity (8) and a separate cavity (10) that houses a cooling fan and is separated from the first cavity by a partition wall (9). The arrangement includes a body (13) made of highly heat-conductive metal, which passes through the partition wall (9) and has ends (17, 18) introduced in the cooking cavity (8) and the separate cavity (10), respectively. The arrangement also includes a heat-sink provision (19, 28, 32) connected with the end (18) of said metal body (13), and three temperature sensors (21, 22, 26) that are adapted to measure the temperatures of said two ends (17, 18) and the cooking cavity (8), respectively. These sensors are further connected with a microprocessor means (25) to supply it with information related to the temperatures they measure, so as to enable the microprocessor means (25) to determine the humidity contents of the air in the oven upon reaching the water-vapor condensation temperature at the end (17) of said metal body.

7 Claims, 3 Drawing Sheets

ARRANGEMENT FOR MEASURING MOISTURE IN OVENS, IN PARTICULAR FOOD COOKING OVENS

BACKGROUND OF THE INVENTION

1. Field of the Invention

This invention relates to an arrangement for measuring the humidity in ovens in general, and in particular in food-cooking ovens, so as to regulate the degree of humidity to a pre-determined level during food cooking processes performed in the oven.

2. Description of Related Art

Food-cooking ovens are known from the prior art to be constituted substantially by a box-like outer casing delimiting an inner cooking cavity in which food to be cooked is arranged. A forced circulation of hot air is brought about in said cooking cavity through a gas-fuelled or electric heat generator and a fan. Some ovens are also provided with a steam generator for steam cooking.

Such ovens are equipped with appropriate thermostatic control systems to regulate the food cooking temperature. Associated temperature selector means are set at the desired temperature value before starting any cooking process to be performed in accordance with the kind and amount of food to be cooked. The thermostatic temperature control systems equipping said ovens operate to keep the food cooking temperature within pre-defined limits inside the cooking cavity, in general, by energizing and de-energizing the heat generator and/or the steam generator, and the air-moving fan, so as to vary in an appropriate way the flow of air circulating through the cooking cavity.

These ovens, however, are not provided with any arrangement for regulating the humidity of the air inside the cooking cavity, a factor that, in conjunction with the temperature, definitely affects the quality of the cooking results and the taste and flavor of the food items being cooked. Humidity is variable depending on various parameters of the cooking process such as the cooking temperature, the kind and the amount of the food to be cooked, the air replacement rate in the cooking cavity, etc. Thus, these appliances do not enable optimal food cooking results to be achieved.

Humidity measurement devices are known in connection with applications of a different kind. These are generally constituted by semiconductor sensing means which are arranged in the moist environment to be controlled and are connected with electrical bridge-type measurement circuits that are adapted to detect the corresponding electric quantities generated by said sensing means and to automatically convert them into corresponding humidity levels prevailing in said moist environment.

Other humidity measuring devices are constituted by elements measuring the concentration of oxygen in gas mixtures, such as for instance in the case of zirconium oxide cells, according to known principles of operation.

However, all of these humidity measurement devices, while ensuring correct and accurate measurements, are on the other hand scarcely suited to measure the humidity under typical food cooking temperature conditions, which usually range from 100° C. through to 250° C. according to the type and the amount of food to be cooked. Said devices would either become damaged, and therefore would be prevented from performing their function, or they would not be able to ensure an adequately reliable operation, since their sensing elements would be subject to soiling.

SUMMARY OF THE INVENTION

It is, therefore, a purpose of the present invention to eliminate all these drawbacks and limitations of the above cited humidity measurement devices by providing an arrangement for the measurement of humidity which, based on a different physical principle, is capable of simply and reliably detecting the levels of humidity prevailing in ovens, and in particular food cooking ovens, in which the food items are usually cooked under relatively high temperature conditions, while at the same time enabling such a humidity to be regulated at pre-set levels so as to perform high-quality cooking processes, no matter which kind and amount of food items are actually involved.

BRIEF DESCRIPTION OF THE DRAWINGS

Such an arrangement for measuring the humidity is substantially provided with the features and characteristics as recited in the appended claims. It will, however, be illustrated in closer details in the following description, which is given by way of nonlimiting example with reference to the accompanying drawings in which:

DETAILED DESCRIPTION OF THE PREFERRED EMBODIMENTS

Figure 1:
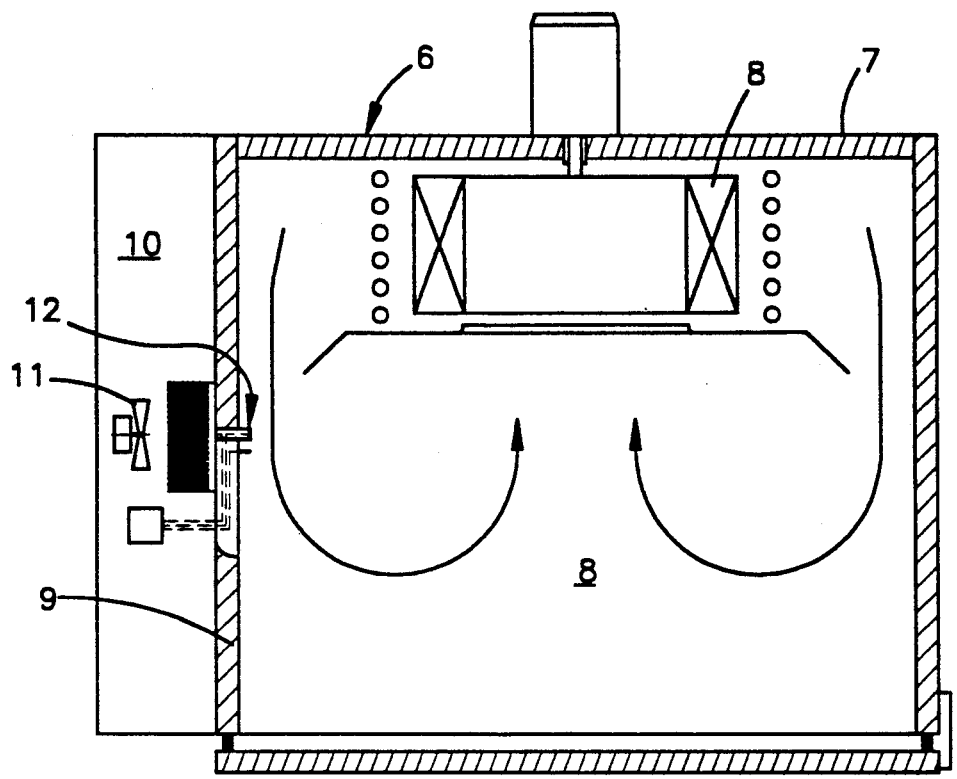
FIG. 1 is a schematical view of a cooking oven provided with the humidity measurement arrangement according to the present invention.

FIG. 1, shows schematically a food cooking oven 6 featuring forced circulation of hot air generated by appropriate gas-fuelled or electric heat generators of some known type (not shown). Alternatively, the oven may include cooking modes which utilize steam alone; combined hot air and steam; microwaves alone; combined microwave, hot air, and steam; or other known types. The oven includes a metal box-like outer casing 7 delimiting an inner cooking cavity 8 in which the food items to be cooked are arranged. The oven is equipped with a fan 5 for said forced circulation of the hot air. The cavity in this particular case (in which the oven with forced hot-air circulation is specially considered) is divided internally by a sheet-metal lined partition wall 9 into a further cavity 10 communicating with the cavity 8 and housing a fan 11 whose function will be described below.

The oven being considered here further comprises a humidity measurement arrangement 12, which is housed in the cavities 8 and 10. The measurement arrangement is built and operates as described in detail hereinafter.

Figure 2:
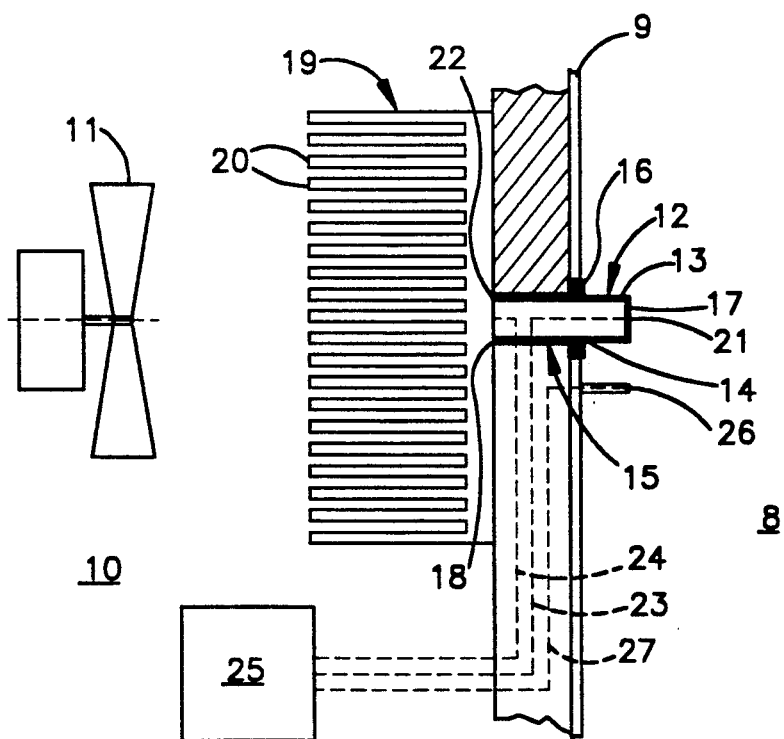
FIG. 2 is a schematical, detailed, front elevation view of the humidity measurement arrangement according to the present invention, in a first embodiment thereof.

FIG. 2 shows schematically the humidity measurement arrangement 12 according to the present invention, in a first possible embodiment thereof.

As can be seen in FIG. 2, said humidity measurement arrangement consists substantially of at least one body 13 made of highly heat-conductive metal of a suitable shape which is inserted through a corresponding through-passing hole 14 that is made in the partition wall 9 separating the cooking cavity 8 from the cavity 10 that houses the fan 11. Said heat-conductive metal body 13 is preferably constituted by an internally hollow copper body. An outer surface 15 of the body 13 is separated from the sheet-metal material of the partition wall 9 by means of a small bushing 16 made of a known heat-insulating material, or by means of some other separating element of similar material, which is inserted through the peripheral edge of said sheet-metal delimiting said through-passing hole 14.

Furthermore, the heat-conductive metal body 13 is enclosed by a small metal bottom plate 17 at one end penetrating for a short length into the cooking cavity 8 of the oven, and is further enclosed by a similar small metal bottom plate 18 at its opposite end. The latter metal bottom plate 18 extends into the other cavity 10 of the oven and is connected to or integrally made with a highly heat-conductive metal element acting as a heat-sink. In this particular case the heat sink is constituted by a metal rectilinear plate 19 which is applied at a right angle against the corresponding outer surface of the small bottom plate 18 and is provided with a plurality of separate fins 20 directed toward the fan 11. The fins 20 are arranged so as to be contacted by the flow of air generated by the fan 11, in view of causing the entire surface of the plate 19, and hence the respective end of the metal body 13 defined by the small bottom plate 18, to gradually cool down.

At least two temperature sensors are applied inside said metal body 13, preferably in the form of thermocouples. A first thermocouple 21 is applied against the inner surface of the end bottom plate 17 and a second thermocouple 22 is applied against the inner surface of the opposite end bottom plate 18. Said thermocouples are connected, through respective electrical lead wires 23 and 24 passing through the inner cavity of said metal body 13, with an appropriate oven control device. In a most advantageous way, the oven control may be made in the form of an electronic microprocessor 25 housed in an appropriate, separate site of the oven to perform the functions that will be further described hereinafter.

The humidity measurement arrangement is further constituted by at least one additional temperature sensor, preferably in the form of another thermocouple 26, which penetrates partially into the cooking cavity 8 of the oven through the afore-cited partition wall 9. The thermocouple 26 detects the temperature of the hot air circulated through said cooking cavity. The temperature sensor 26 is connected at its free end with said electronic microprocessor 25 through a respective electrical lead wire 27.

In this way, the described arrangement of the temperature sensors 21, 22 and 26 enables not only a cooking temperature T1 of the food items in the cooking cavity 8 to be measured through said temperature sensor 26, but also temperatures T2 and T3 of the end bottom plates 17 and 18 of said metal body 13 to be measured through the respective temperature sensors 21 and 22. The temperature T2 of the end bottom plate 17, is in particular subject to direct contact with the hot air circulated in the cooking cavity 8, and is higher than the temperature T3 of the end bottom plate 18 which on the contrary is cooled down by the heat-conductive contact with the metal heat-sink element 19.

It therefore ensues that, as the end bottom plate 18 is gradually cooled down by said heat-sink element 19, the end bottom plate 17 of said metal body 13, owing to heat conduction through said metal body 13, also tends to cool down gradually, albeit more slowly because said end bottom plate 17 is on the other hand continuously heated up by the hot air in the cooking cavity 8.

The end bottom plate 17, while undergoing such a simultaneous heating-up and cooling-down process, will eventually reach a thermal equilibrium wherein the humidity present in the air of said cooking cavity is caused to condense on the same bottom plate 17 upon reaching the respective condensation temperature, or dew point, so that condensate builds up on the outer surface of said bottom plate. Then, the temperature sensor 21 that is associated therewith will immediately detect said temperature T2 and convey the corresponding information to the electronic microprocessor 25, which will in turn determine the respective measurement value, along with the measurement values relating to both the temperature T3 of the end bottom plate 18 and the temperature T1 of the cooking cavity 8, which are detected by the temperature sensors 22 and 26, respectively.

As a consequence, on the basis of the measured values of the temperatures T1, T2 and T3 detected in the afore-described way, the humidity measurement arrangement according to the present invention is capable of automatically and instantaneously determining the humidity content of the air inside the oven, in correspondence of the afore-cited dew point. The arrangement takes advantage of the physical principle according to which in a gas mixture also containing water vapor (such as in the case of the moist air contained in the cooking cavity of the oven), said water vapor will fully condense in correspondence of its dew point, which is a variable quantity depending on the ambient pressure, whereas the remaining gaseous mixture will not be condensable, so that it will remain in its gaseous state. It should further be noticed that this condensation temperature, or dew point, is also dependent on the humidity content of the gaseous mixture.

Figure 5:
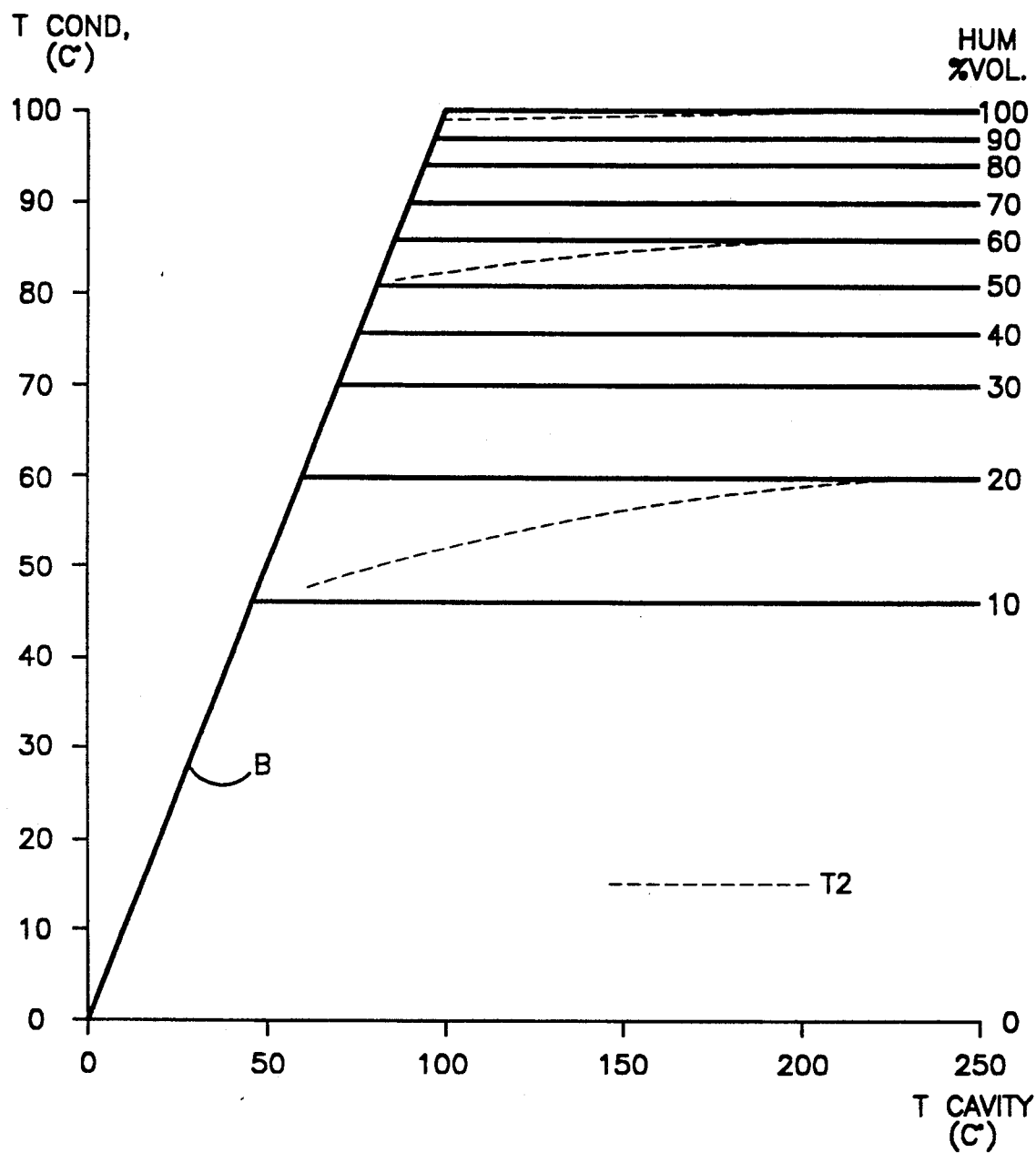
FIG. 5 plots a temperature-humidity chart for a food cooking oven as the one shown in FIG. 1, which is shown here to better understand the principle of operation on which the humidity measurement arrangement according to the present invention is based.

FIG. 5 illustrates a chart which should be used in order to better understand the operation of the humidity measurement arrangement according to the present invention. This chart indicates on the ordinates the condensation temperature, or dew point, of water vapor contained in a gaseous mixture, i.e. in this particular case the moist air contained in the cooking cavity of the oven. The ambient heating-up temperature is indicated in the abscissae, i.e. in this particular case the food heating-up temperature in the cooking cavity of the oven.

This chart has been plotted with reference to a constant ambient pressure, i.e. in this particular case the pressure of the ambient air, on the basis of the Mollier diagram for moist air, and extrapolating the corresponding values of the condensation temperature, or dew point, at said constant pressure.

The water vapor heating-up temperatures in the cooking cavity of the oven turn out in general to be situated anywhere between ambient temperature and a highest possible value of approx. 250°. Thus, based on said extrapolated values it is possible to determine, for said constant ambient pressure, the condensation temperature, or dew point, of said water vapor, i.e. in this particular example for temperatures situated anywhere between the ambient temperatures and 100° C., as a function of its humidity content.

As determined theoretically through the afore-cited extrapolation, the humidity contents in percent-volume of water vapor corresponding to respective condensation temperatures, are indicated with straight horizontal lines running parallel to each other, each one of them duly marked with the respective humidity content. The straight inclined line B, which starts from the point 0 where the cartesian axes meet, defines the delimitation zone between the air-water vapor mixture in its gaseous state (on the right side with respect to said straight line) and the condensed water vapor, i.e. in its liquid state, (on the left side with respect to said straight line.)

As a consequence, by measuring the temperature T2 of the end bottom plate 17 of the metal body 13 (corresponding to the condensation temperature, or dew point, of the water vapor), the food heating-up temperature T1 in the cooking cavity of the oven, and the temperature T3 of the other end bottom plate 18 of said metal body 13, which shall in all cases be detected since it is variable according to the heat-sink element 19 that is used, it is possible to determine the respective humidity content in percent-volume of the water vapor contained in the cooking cavity on the basis of the aforementioned temperature-humidity contents diagram.

However, in the course of practical experimental work that has been carried out in this connection, it has been ascertained that, for equal heating-up temperatures, the humidity contents of the water vapor contained in the cooking cavity of the oven are reached with condensation temperatures that are different and lower than those determined theoretically and represented with straight horizontal lines on the chart.

As a matter of fact, during the above mentioned practical experimental work it has been observed that humidity contents have a tendency to progress in the form of curved lines that become gradually straight as the heating-up temperatures increase. The difference, shown in FIG. 5, is due to the fact that the gradual stratification of the water vapor on the end bottom plate 17 of said metal body 13, as a consequence of the gradual cooling-down of the same end bottom plate due to heat dissipation, has the effect of thermally insulating the metal of said plate and said body, thereby causing the respective sensor 21 for the temperature T2 to detect temperatures that are lower than the actual condensation temperatures.

As a consequence, by knowing beforehand the experimentally determined configuration of these curves for the various actual values of the humidity content, it is possible to store these actual values, in an appropriately coded form, in the memory of the microprocessor 25, along with the corresponding condensation temperatures, or dew points, of the water vapor.

Furthermore, the values of both the temperature T3 of the cooled-down end bottom plate 18 of said metal body 13 and the food cooking temperature T1 will have been preliminarily stored, in an appropriately coded form, in the memory of said microprocessor. The microprocessor is programmed to receive temperatures T3 and T1, as detected by the respective sensors 22 and 26, and the above mentioned temperature T2, and immediately recognize the temperatures to determine the corresponding condensation temperature of the water vapor and, hence, the humidity content of the air contained in the cooking cavity of the oven. In this manner, the microprocessor automatically measures the humidity content of the air contained in the cooking cavity of the oven and, at the same time, is also capable of causing said humidity content to be regulated to pre-set values that will have been selected manually by means of appropriate selectors equipping the oven and associated with said microprocessor. By continuously comparing the actual humidity values with the pre-set ones that have been previously stored in a coded form in the memory of said microprocessor, the arrangement is capable of acting on the various functional component parts of the oven (i.e. heat generator, steam generator, etc.) until the desired humidity content, corresponding to the one that has been pre-set through said selectors, is actually reached in the cooking cavity.

The inherent advantages of the humidity measurement arrangement according to the present invention are at this point fully and clearly apparent. As a matter of fact, thanks to the simplicity of its construction and the practical absence of parts that may be impaired or damaged by the high cooking temperatures of the ovens, the humidity measurement arrangement according to the present invention may be used to both measure humidity under any cooking temperature condition, in a very reliable way and to a very accurate extent, and to carry out cooking processes under pre-set and variable humidity level conditions. The humidity levels can be appropriately selected by the user in accordance with the amount and the kind of food items to be cooked, so as to bring about optimal cooking processes for the food items, by keeping their flavor and properties nearly unaltered, and enable the operation, performance, and efficiency of the cooking ovens to be rationalized.

Figure 3:
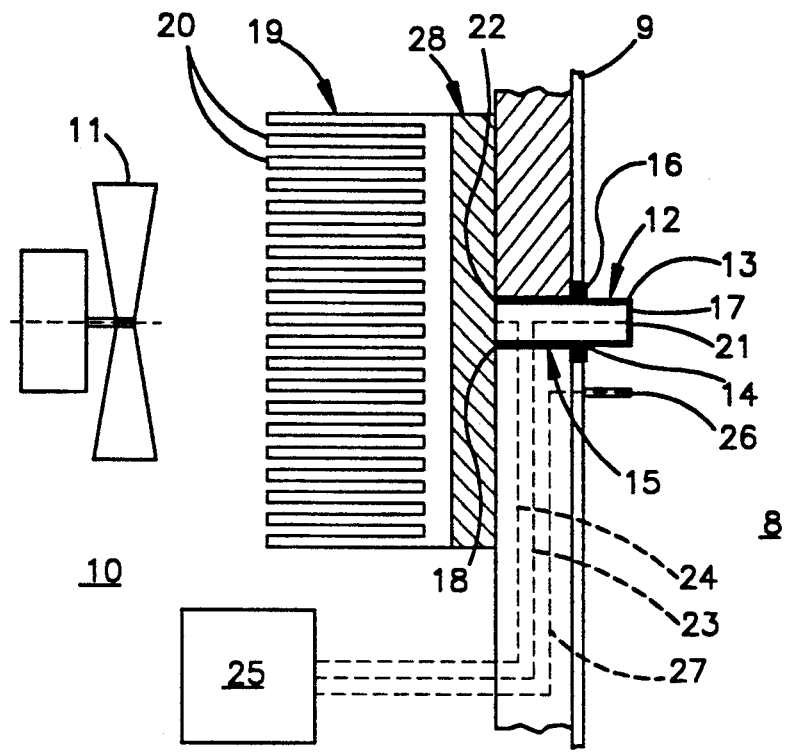
FIGS. 3 and 4 are schematical, detailed, front elevation views of the humidity measurement arrangement according to the present invention, referring to two further possible embodiments thereof.

FIG. 3 shows a second possible embodiment of the humidity measurement arrangement according to the present invention. The metal body 13 is unchanged with respect to the afore described embodiment, the heat-sink provision used in this case is provided in the form of a battery of known Peltier elements 28, which is also provided with separate fins 20 arranged so as to face the fan 11 and to be cooled by the flow of air generated by the same fan.

Figure 4:
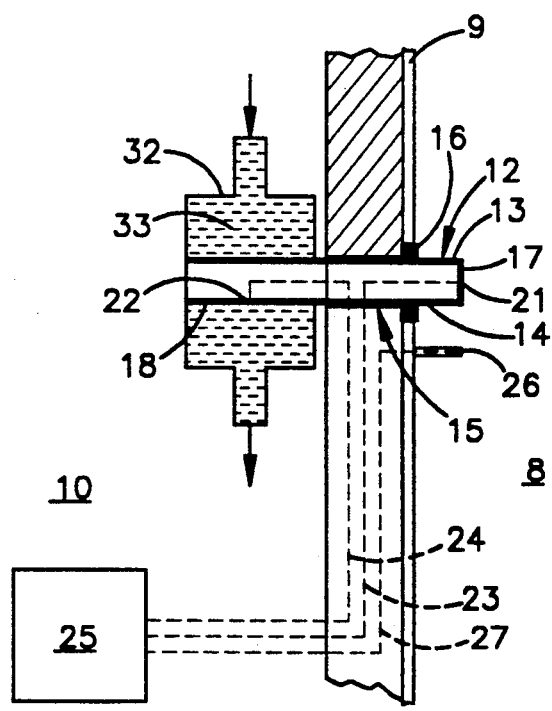

Finally, FIG. 4 shows a further possible embodiment of the humidity measurement arrangement according to the present invention. Around the terminal portion of the metal body 13 and the corresponding end 18, which are inserted in said separate cavity 10 of the oven, an innerly hollow cool-down metal element 32 is applied in tight contact therewith. The hollow section 33 thereof is being such as to enable an appropriate cooling medium 34 from a separate supply source (not shown) to be circulated therein.

It will be appreciated that other embodiments of the humidity measurement arrangement, which may differ from the ones that have been described here by way of non-limiting examples, may possibly be conceived and provided to the same purposes and aims as cited above, without departing from the scope of the present invention.

Similarly, this humidity measurement arrangement may be used not only in cooking ovens, but also in ovens or heating equipment of a different purposes or applications, such as for instance in laboratory equipment operating under controlled humidity conditions, without departing from the scopes of the present invention.

What is claimed is:

1. A humidity measurement arrangement for a heating appliance, comprising a cooking cavity for items, a further cavity in communication with the cooking cavity and separated therefrom, a partition wall separating the cavities, heat generating means, and a fan associated with the heat generator for forced-convection hot-air cooking of the items, said fan being accommodated in said cooking cavity, characterized by a highly heat-conductive metal body (13) which is inserted through said partition wall (9) and is thermally insulated from the same wall, so as to be inserted with a first end (17) thereof in said cooking cavity (8) and with a second end (18) thereof in said further cavity (10); heat-sink means (19, 28, 32) communicating with said second end and arranged within said further cavity (10); first and second temperature sensor means (21, 22) associated with said first and second ends (17, 18); third temperature sensor means (26) inserted in said cooking cavity (8); and control means (25) connected with said first, second, and third temperature sensors, said control means (25) including an electronic microprocessor, and being capable of storing coded information corresponding to the range of temperatures that can be reached in correspondence of said first and second ends (17, 18) and said cooking cavity (8), and being further arranged so as to automatically determine, on the basis of the temperature levels measured at the same time by said first, second and third temperature sensor means (21, 22, 26) in correspondence of the dew point of water vapor in the air inside said cooking cavity (8) as measured by means of said first sensor means (21), the humidity content of the same air, said control means (25) being also arranged to automatically regulate said humidity content of the air to pre-set variable levels that are selected by means of selector means associated with said control means (25).

2. Humidity measurement arrangement according to claim 1, characterized in that said metal body (13) is preferably made of copper and is innerly hollow.

3. Humidity measurement arrangement according to claim 1, characterized in that said first and second ends (17, 18) of said metal body (13) are closed by means of respective bottom plates.

4. Humidity measurement arrangement according to claim 3, characterized in that said first and second sensor means (21, 22) are applied against inner surfaces of the respective bottom plates of said first and second ends (17, 18).

5. Humidity measurement arrangement according to claim 4, characterized in that said heat-sink means comprise a metal plate (19) connected with the bottom plate of said second end (18) and provided with a plurality of separate fins (20) that are arranged so as to be facing a cooling fan (11).

6. Humidity measurement arrangement according to claim 5, characterized in that said heat-sink means comprise Peltier elements (28), provided with a plurality of separate fins (20) that are arranged so as to be facing a cooling fan (11).

7. Humidity measurement arrangement according to claim 6, characterized in that said heat-sink means comprise an innerly hollow metal cooling element (32), arranged tightly around the terminal portion of said metal body (13) and the respective end bottom plate (18) thereof, and a cooling medium (34) circulated in the hollow section (33) of said cooling element (32).

* * * * *

UNITED STATES PATENT AND TRADEMARK OFFICE
CERTIFICATE OF CORRECTION

PATENT NO. : 5,272,963
DATED : December 28, 1993
INVENTOR(S) : Claudio Del Fabbro It is certified that error appears in the above-identified patent and that said Letters Patent is hereby corrected as shown below:

Column 8, Claim 1, line 1, after "pre-set" insert --and--.

Signed and Sealed this

Twenty-eighth Day of June, 1994

Attest:

BRUCE LEHMAN

*Attesting Officer*     *Commissioner of Patents and Trademarks*